United States Patent [19]

Wautier

[11] Patent Number: 5,071,956
[45] Date of Patent: Dec. 10, 1991

[54] PROTEIN WITH VASCULAR ACTIVITY DERIVED FROM MONOCYTES AND ITS ANALOGUES, A PROCESS FOR ITS EXTRACTION AND THEIR USES FOR THERAPEUTIC PURPOSES AND FOR THE PREPARATION OF ANTIBODIES

[75] Inventor: Jean-Luc Wautier, Paris, France

[73] Assignee: Institut des Vaisseaux et du Sang, Paris, France

[21] Appl. No.: 230,352

[22] Filed: Aug. 10, 1988

[30] Foreign Application Priority Data

Aug. 12, 1987 [FR] France ............................. 87 11490

[51] Int. Cl.$^5$ ..................... C07K 3/00; A61K 37/02
[52] U.S. Cl. .................................. 530/329; 530/327; 530/350; 530/395
[58] Field of Search ............... 530/329, 327, 350, 395; 514/8, 14, 17, 21

[56] References Cited

PUBLICATIONS

Henson et al, "Tissue Injury in Inflammation" J. Clin. Invest., vol. 79, Mar. 1987, 669–674.
Heimark et al, "Inhibition of Endothelial Regeneration by Type-Beta Transforming Growth Factor from Platelets" Science, vol. 233, Sep 5, 1986, 1078–1080.
Glenn et al, "Human Monocyte-Derived Growth Factor(s) for Mesenchymal Cells" Cell, vol. 25, 603–615, Sep. 1981.
Martinet et al, "Activated Human Monocytes Express the C-SIS Proto-Oncogene and Release a Mediator Showing PD6F-like Activity" Nature, vol. 319, Jan. 9, 1986, 158–160.

*Primary Examiner*—Nathan M. Nutter
*Attorney, Agent, or Firm*—Larson and Taylor

[57] ABSTRACT

This invention has as its object a protein, preferably a glycosylated protein, having a molecular weight of about 0.6 to 200 kD, containing the following sequence which is in particular N-terminal:

-Ser-Pro-Glu-Leu-Thr-Phe-, preferably:

-Ser-Pro-Glu-Leu-Thr-Phe-Arg-X-Y-Thr-Ile-Ser-, where X and Y, which may be identical or different, each represent Trp or Asp.

It relates in particular to a glycoprotein derived from monocytes (MECIF) and having an apparent molecular weight of 64–70 kD and containing 568 amino acid residues.

Application in particular to the treatment of diabetic retinopathies, neovascularisation, arteritis, venous disorders, vascular tumors and rheumatoid arthritis.

4 Claims, No Drawings

PROTEIN WITH VASCULAR ACTIVITY DERIVED FROM MONOCYTES AND ITS ANALOGUES, A PROCESS FOR ITS EXTRACTION AND THEIR USES FOR THERAPEUTIC PURPOSES AND FOR THE PREPARATION OF ANTIBODIES

This invention relates to a family of proteins, in particular glycoproteins, which have a vascular activity, inhibiting the proliferation of endothelial cells, in particular a factor derived from monocytes, to a process for the extraction of this factor and to the applications of these proteins.

The control of vascular cell growth is an important factor in the genesis and development of atherosclerosis and neoangiogenesis. Particular attention has recently been directed to the growth factors which stimulate the proliferation of endothelial cells, the cells of smooth muscles and fibroblasts. Only a small number of factors capable of inhibiting the proliferation of vascular cells have been identified.

Numerous research workers have recently concentrated their attention on the role of the monocytes in the circulation for regulating the growth of the cells of blood vessel walls. The participation of monocytes in numerous pathological processes affecting the walls of blood vessels, such as vasculatidis, atherosclerosis, inflammation and cancerous metastases has recently been reported (references 1 and 2). The factors controlling growth play important roles in such cases. Monocyte-derived Growth Promoting Factors, also referred to as MDGF, have been isolated and identified (references 3 to 11).

The results of preliminary work carried out by the present Applicant (reference 12), which agree with the results obtained by Kahaleh and coworkers (reference 13), show that in addition to the growth promoting factors, monocytes are also capable of producing inhibitory factors.

The Applicant has in particular established that normal human monocytes produce a factor which inhibits the proliferation of human endothelial cells, and has named this factor MECIF (Monocyte-derived Endothelial Cell Inhibitory Factor).

The applicant has now developed a process for extracting MECIF to such a degree of purity that this substance can be analysed.

According to one of its aspects, the invention has as its object a process for the extraction of a monocyte-derived endothelial cell inhibitory factor, or MECIF, characterised in that it basically comprises the following stages:

1°) Cultivating normal human monocytes,
2°) passing the filtered supernatant layer of culture through a column of cross-linked polysaccharide equilibrated at about pH 8,
3°) then passing the supernatant layer through a column of phenylated and cross-linked agarose gel equilibrated at about pH 8, employing the technique of decreasing gradient elution using ammonium sulphate,
4°) passing the active fractions obtained under 3°) through a column of the type used under 2°) equilibrated at about pH 8,
5°) passing the eluate obtained under 4°) through an ion exchange column of the diethylaminoethyl type (DEAE), with increasing gradient elution using sodium chloride,
6°) passing the fractions obtained under 5°) through a low pressure exclusion chromatographic column equilibrated by means of a cell culture medium and
7°) collecting the purified product, optionally after having subjected the active fractions obtained under 6°) to high pressure liquid chromatography.

The normal human monocytes are isolated from blood either by differential centrifuging or by cytapheresis and selective adhesion in plastic dishes which may or may not be covered with fibronectine. Details of this technique are described in the experimental part given hereinafter.

The monocytes are advantageously cultivated for about 24 hours.

The column of cross-linked polysaccharide may be, for example, of the type marketed under the name of Sephadex ® G-25 by the pharmaceutical company, Pharmacia Fine Chemicals (Uppsala, Sweden).

The column of phenylated and cross-linked agarose gel may be, for example, of the type marketed by the same Company, Pharmacia under the name of Phenyl Sepharose ® Cl 4B.

The DEAE type of ion exchange column may be, for example, that marketed under the name of DEAE-Trisacryl ® LS by IBF (Gennevilliers, France).

The low pressure exclusion chromatographic column may be, for example, that marketed by IBF under the name of Trisacryl ® GF-05.

High pressure liquid chromatography (HPLC) may be carried out using a column marketed under the name of TSK-250 by Bio-Rad (Munich, Federal Republic of Germany).

A detailed, non-limiting example of carrying out this process is given in the experimental part of this specification to explain the process more fully.

According to one variation, the MECIF may be isolated from the supernatants of leukaemic monocytoid cellular lines such as the line HL 60 (reference 14), after stimulation with retinoic acid or better still with DMSO.

MECIF and its derivatives which will be mentioned later may also be obtained by genetic engineering techniques, from the known peptide sequence, with isolation of the corresponding mRNA.

From analysis of the purified MECIF obtained, it has been possible to establish that it is a glycoprotein with an apparent molecular weight of 64–70 kD.

This glycoprotein contains 568 amino acid groups or residues distributed in approximately the following proportions: Asp: 80; Thr: 23.06; Ser: 29.40; Glu: 56.5; Pro: 27.70; Gly: 38.98; Ala: 42.88; Val: 36.16; Met: 4.83; Ile: 18.79; Leu: 50.92; Tyr: 20.15; Phe: 27.16; GlcNH$_2$: 3.10; Lys: 60.87; His: 13.81; Arg: 27.60.

Its N-terminal peptide sequence is as follows:

Ser-Pro-Glu-Leu-Thr-Phe-Arg-X-Y-Thr-Ile-Serwhere X and Y, which may be identical or different, each represent Trp or Asp.

This glycoprotein contains amino sugars and non-amino sugars.

It is stable in storage for 2 months at 4° C. or for longer periods at −80° C. or in a lyophilised form.

. The glycoprotein thus defined constitutes a further object of this invention.

The invention also has as its object a protein, preferably a glycosylated protein, with a molecular weight between about 0.6 and 200 kD containing the sequence:

-Ser-Pro-Glu-Leu-Thr-Phe-.

This sequence is preferably N-terminal.

Moreover, the sequence in question is preferably as follows:

-Ser-Pro-Glu-Leu-Thr-Phe-Arg-X-Y-Thr-Ile-Serwhere X and Y, which may be identical or different, each represent Trp or Asp.

X and Y preferably differ and, more preferably, X denotes Trp and Y Asp.

Such a protein is advantageously prepared by conventional techniques of genetic engineering.

MECIF acts on human endothelial cells at concentrations of the order of a picogramme per millilitre and has little activity on the endothelial cells of pigs. It does not substantially modify the growth of smooth muscle cells or cells of human arteries, or fibroblasts of adult skin or fibroblasts of embryonic lung.

Its action on human endothelial cells is detectable after 6 hours of contact. It reaches a plateau at the end of 12 hours and is stable for 48 hours.

Its action is partially reversible (50%) by the addition of a growth factor (ECGF: Endothelial Cell Growth Factor).

MECIF is not cytotoxic at a concentration of 5 mg/ml.

MECIF and the (glyco)proteins derived therefrom as defined above and having the same properties may be converted in the presence of conventional additives and/or excipients into galenic forms for local cutaneous application, intra-articular injection, subcutaneous injection or intravenous perfusion or, in particular, as eye lotions or ointments.

MECIF and derivatives thereof which have the same properties may be used therapeutically, in particular:

in ophthalmology for the treatment of diabetic retinopathies, neovascularisation and senile macular degeneration;

for the treatment of peripheral vascular diseases or arteritis, and the prevention of obstruction of prostheses by endothelial proliferation;

for the treatment of venous diseases to prevent the proliferation of neocapillaries and the treatment of venous disorders of the lower limbs and acne rosacea;

for the treatment of vascular tumor diseases; angiomata with vascular proliferation, Kaposi's syndrome and tumorous neoangiogeneses (solid tumours, kidneys, liver . . . );

for the treatment of inflammatory diseases: rheumatoid arthritis.

The form and dose of administration depend mainly on the disorder to be treated and the particular characteristics of the patient and may be determined by the man of the art on the basis of his conventional knowledge.

MECIF may also be used to produce, by conventional techniques, specific polyclonal or monoclonal antibodies which may be used to determine the levels of MECIF in vascular and tumour, rheumatic and inflammatory pathology.

The ELISA technique may advantageously be employed for this purpose, in particular as described in reference 15.

The derivatives of MECIF described above may also be used to produce antibodies.

The detailed description given below of an example of extraction of MECIF and its physico-chemical and pharmacological study is given to explain the invention more fully without limiting its scope.

EXPERIMENTAL PART

I. Preparation of a supernatant layer of monocyte culture:

A sample of citrated complete human blood from normal donors in good health is used. The mononuclear cells are first separated by density gradient centrifugation and the monocytes are then isolated by a method of selective adhesion, that is to say by inoculating culture dishes of plastics material with the mononuclear cells (reference 16). The adhered mononuclear cells recovered after this procedure comprise $95\pm3\%$ of monocytes according to the specific stain test with esterase and labelling of the cells with specific monoclonal antibodies for monocytes and lymphocytes (reference 16). The contamination with platelets amounts to between 5 and 10 platelets per monocyte.

The monocytes are then incubated in a M-199 culture medium supplied from GIBCO with the addition of 2.5% of foetal calves serum (FCS) for 24 hours at 37° C. in an atmosphere of 5% of $CO_2$. At the end of this period, the supernatant of the culture is collected and filtered through a filter with a porosity of 0.2 μm. All the above stages are carried out under sterile conditions. Note: The effects of various chemical products on the production of MECIF were studied by adding these products to the monocytes at the start of the incubation period.

II. Purification of the protein:

Materials

The chromatographic supports, Sephadex ® G-25 and Phenyl Sepharose ® CL4B are supplied by Pharmacia Fine Chemicals (Uppsala, Sweden), DEAE-Trisacryl ® LS and Trisacryl ® GF-05 are supplied by IBF (Gennevilliers, France) and the HPLC column TSK-250 is supplied by Bio-Rad (Munich, Federal Republic of Germany). All the chemical products used are of "reagent" quality.

At each stage of the process of purification, each fraction is tested in triplicate in the test for endothelial cell proliferation to detect the fraction containing the inhibitory activity.

Several portions of one liter of the supernatant of the culture of monocytes are passed in separate tests through a column of Sephadex G-25 (4.4×70 cm) which is equilibrated with 10 mM Tris buffer, pH 8.0. The active fractions which have been collected are then treated with a 30% saturated solid ammonium sulphate and, after centrifuging, the supernatant layer is passed through a column of Phenyl Sepharose (3.2×33 cm) equilibrated with 10 mM Tris buffer, pH 8.0 containing 30% saturated ammonium sulphate. After the sample has been set up and thoroughly rinsed with equilibrating buffer, the column is developed with a linear gradient of ammonium sulphate ranging from 30 to 0%, in 10 mM Tris buffer, pH 8.0. The active fractions are collected and passed through a column of Sephadex G-25 as described above, before an additional separation is carried out by means of a DEAE Trisacryl-LS column (1.5×8 cm) with a linear gradient of NaCl ranging from 0 to 1M in a 10 mM Tris buffer, pH 8.0. Before the chromatograph fractions are examined for their biological activity on the vascular culture cells, they must all be passed through a column of Trisacryl GF-05 (2.4×10 cm) equilibrated with a culture medium, namely Hanks buffer (supplied by the Pasteur Institute, Paris, France). The final purification factor up to chromatography on the GF-05 column is 570 times. To verify that the protein isolated after the chromatographies on the DEAE and GF-05 columns is the MECIF protein and to determine the molecular weight of this protein, the active fraction is then subjected to another process of chromatography on a HPLC TSK-250 column and analysed by SDS PAGE electrophoresis (sodium dodecyl sulphate-polyacrylamide gel electrophoresis).

The concentration of protein is determined on the pure fraction from the composition of amino acids and by measurement with the auto-analyser.

The amino acid composition given above is determined by means of a sequencer.

Analysis with the autoanalyser of a sample of product has enabled the following concentrations of amino acids to be determined (values in picomols): Asp: 20.079; Thr: 5.79; Ser: 7.38; Glu: 14.18; Pro: 6.95; Gly: 9.78; Ala: 10.764; Val: 9.078; Met: 1.212; Ile: 4.716; Leu: 12.781; Tyr: 5.058; Phe: 6.819; GlcNH$_2$: 0.778; Lys: 15.279; His: 3.48; Arg: 6.92.

The approximate numbers of the different amino acid groups indicated above were deduced from the results.

III. Test of cellular culture and proliferation:

Human vascular endothelial cells are collected from an umbilical cord and cultured by a technique previously described (reference 17). The fibroblasts of human skin and of embryonic lung are a gift of A. Macieira Coehlo (INSERM U-50, Villejuif, France) and the cells of human femoral smooth muscles are a present from J. Larrue (INSERM U-8, Pessac, France). The endothelial cells of pigs aorta were supplied by L. Drouet (INSERM U-150, Paris, France). The (methyl-$^3$H)-thymidine (5 Ci/mmol) was obtained from the Commissariat à l'Energie Atomique, France. The vascular culture cells labelled with thymidine were collected by means of a cell harvester (Skatron, Lier, Norway).

The biological activity of MECIF was tested in triplicate by the incorporation of (methyl-$^3$H)-thymidine in the DNA of a vascular cell culture. For this purpose, 12 to 15,000 cells in a M-199 culture medium with the addition of 10% of foetal calves serum are introduced into each culture well of a multiple well dish and incubated for 24 hours at 37° C. in the presence of MECIF in an atmosphere of 5% of $CO_2$. The cultivated cells are then incubated for 16 hours with (methyl-$^3$H)-thymidine (1 μCi/well). At the end of this time, the medium is removed and after exposure to collagenase, the cells are collected on glass fibre filters, using a cell harvester. The human and porcine endothelial cells employed for the study of proliferation were obtained from primary cultures, while the smooth muscle cells and fibroblasts were obtained from eighth and thirteenth passages, respectively.

Results:

Production of MECIF by a culture of normal human monocytes:

It has been found that the isolated monocytes of human blood liberate a factor called as MECIF which is capable of inhibiting the proliferation of endothelial cells of the human umbilical vein, as demonstrated by the incorporation of (methyl-$^3$H)-thymidine in these cells. The production of MECIF by monocytes in culture reaches its maximum after 24 hours of incubation and then declines. The MECIF present in the medium after the first 24 hours nevertheless could remain stable for at least 72 hours. The production of MECIF depends on the number of monocytes and the concentrations of serum proteins in the culture medium. The maximum expression of MECIF was observed when the concentration of foetal calves serum in the culture medium for monocytes was 2.5%.

To exclude the possibility that the expression of MECIF is due to contaminant cells, culture media for platelets or lymphocytes at the normal concentrations found in the preparation of monocytes were tested on the endothelial culture cells, using a similar process to that described for the monocytes. The results in contrast showed an increase in the synthesis of DNA in the endothelial cells, suggesting that the production of MECIF is directly attributable to the monocytes.

The treatment of the monocytes culture with cycloheximide completely eliminates the liberation of MECIF in the culture medium. Moreover, treatment with indomethacine, which is an inhibitor of cyclooxygenase, causes no change in the expression of MECIF. This would suggest the necessity of protein synthesis but not of the metabolism of arachidonic acid for the expression of MECIF.

The activation of monocytes with endotoxine [LPS (lipopolysaccharide), *Escherichia coli,* 10 μg/ml] or with fMLP (formyl-methionyl leucine phenylalanine, 0.1 μM) does not promote the production of MECIF.

Storage of a culture medium containing MECIF at 4° C. has no effect on the bioactivity, and the medium is stable for 5 minutes at 56° C.

The bioactivity of MECIF is not neutralised by aprotinine, an inhibitor of protease.

Other observations have shown that MECIF does not exert its bioactivity on endothelial cells by means of a direct cytotoxicity since it does not bring about the liberation of $^{51}$Cr from previously labelled endothelial cells.

Purification of the protein:

After the stage of purification on Phenyl Sepharose, the activity of MECIF on endothelial cells was observed in the peak eluted at about 14% ammonium sulphate. The other fractions showed a negligible activity. The stage of additional purification with the DEAE Trisacryl-LS separated MECIF from the other proteins. The fraction containing MECIF was eluted in the first peak and analysis by electrophoresis on the gel showed that it was a single band.

The activity of this protein was further confirmed as present in the fractions of the single peak after it had been subjected to HPLC TSK-250 chromotography. Furthermore, when the culture medium of monocytes containing crude MECIF was passed through the TSK-250 column, the active fractions were found in the same volume as the active fractions obtained from chromatography on DEAE.

Experiments were also carried out to introduce chromatographies on Heparine Sepharose ® and on Cibacron Blue F3GA Sepharose ® into the process of purification but it was found that MECIF could not be retained by either of these chromatographic supports.

Properties of purified MECIF:

As determined by SDS/PAGE electrophoresis under non-reduced conditions and staining with Coumassie Blue, MECIF which has been purified by chromatography on DEAE-Trisacryl LS migrates in the form of a single, wide band having an apparent molecular weight of 64 kD. Under reduced conditions, it appears in the form of two bands, a major band of about 70 kD and a minor band of about 68 kD. High pressure liquid chromatography with TSK-250 (60×0.75 cm) shows a single peak corresponding to a molecular weight of about 66 kD.

Staining of the electrophoresis gel SDS/PAGE with silver nitrate shows no additional bands such as that obtained with the Coumassie Blue stain. The periodic acid-Schiff reaction (PAS) is positive, which shows that MECIF is a glycoprotein. When the supernatant layer of monocytes is subjected to high pressure liquid chromatography (on TSK-250), the inhibitory activity is found in the fractions (molecular weight: 66 kD) eluted in the same volume as pure MECIF. This shows that MECIF corresponds to the inhibitory activity present in the supernatant of monocytes.

Regulatory activity on growth:

It has been found that the inhibition of the incorporation of (methyl-$^3$H) thymidine depends on the concentration of the culture medium containing the MECIF. Dilution of this medium by 64 times from its original concentration reduces the inhibitory effect by 80 to 30% compared with the control (n=15). A concentration of 14 pg of MECIF produces an inhibitory effect of 81±2.5% (X±SEM; SEM=standard mean error) on the incorporation of thymidine in the presence of foetal calves serum (2.5 to 10%) (n=16). The growth regulatory effects on vascular endothelial cells depend on the concentration of MECIF. At the same concentrations, MECIF does not influence markedly the incorporation of thymidine in fibroblasts of normal human skin (113±5%, n=6) as well as in those of embryonic lung (128±6%, n=8). Under the same conditions, smooth muscle cells and the cells of human arteries are not affected (108±8%, n=12). Inhibition by 28±7% (n=12) is observed with endothelial cells of pig but to a much less extent.

A study carried out over a period of time has shown that the synthesis of DNA is suppressed by MECIF after 6 hours of incubation and this effect reaches its plateau after 12 hours of incubation. Moreover, the inhibitory effect of MECIF on the synthesis of DNA takes place parallel with the reduction of cell proliferation, as was determined by counting the cells under an optical microscope.

Reversibility assay

The endothelial cells were first cultured in the presence of MECIF for 24 hours and then the (methyl-$^3$H) thymidine incorporation to some of the cell culture was measured after 16.72 and 120 hours. Whilst in two other cell cultures, after this 24 hour incubation, the cells were further cultured in the presence of either 20% Fetal Calf serum or 25 μg ECGF (Endothelial Cell Growth Factor) for other 16.72 and 120 hour periods. The results were expressed in percent of the (methyl-$^3$H) thymidine incorporation to these cells at the end of each incubation time, as compared to those cultured in the absence of MECIF.

After the same assay with TGFβ, it was found that reversibility of the endothelial cell growth was easier to be obtained after the exposure of the endothelial cells to MECIF rather than to TGFβ.

Comparative study between TGFβ activity and MECIF activity

As described by the manufacturer (R&G, Minneapolis, Minn., USA) the inventor found that 40 μl (equivalent to 100 μg IgM) specific polyclonal antibodies directed against human TGFβ (R&G) neutralized the biological activity of 2ng/ml TGFβ (Calbiochem, La Jolla, Calif.). Various concentrations (2-12 μg/ml) of intermediate grade purity of MECIF (after DEAE chromatography) were used and the amount which gave 50% inhibition of endothelial cell proliferation was compared to that of TGFβ which also produced 50% of growth inhibition (2 ng/ml). MECIF or TGFβ was incubated with the anti TGFβ for 1 hour at room temperature before to be tested for its inhibitory effects. These anti TGFβ did not neutralize the inhibitory effects of MECIF on the growth of the endothelial cells.

When endothelial cells are observed under an optical microscope, the presence of MECIF in their culture medium brings about morphological changes in the cells, which assume an elongated form. Investigation by immunofluorescence and observations under a transmission electron microscope, however, have shown that the cells preserve their specific markers, that is to say the Willebrand factor and the Weibel Palade bodies.

On the other hand, when TGFβ inhibited the endothelial cell proliferation, it did not alter the cell morphology.

DISCUSSION

The results presented in this experimental part demonstrate the capacity of cultures of normal human monocytes to liberate a factor which inhibits the growth of human endothelial cells. This inhibitory effect is not due to a cytotoxic activity but to the inhibition of DNA synthesis. The factor in question, MECIF, is a glycoprotein having an apparent molecular weight of 66 kD when highly purified. Expression of this factor from crude monocyte extracts depends on the number of monocytes introduced into the culture well and its production implies protein synthesis.

The monocyte origin of MECIF is confirmed by the fact that possible contaminant cells (platelets, lymphocytes) produce no inhibitory action under the experimental conditions but a small proportion of lymphocytes (<10%) could have some influence on the production of the inhibitor by the monocytes.

It has been shown that in its biological properties, the MECIF isolated from the crude monocyte extract is an inhibitory factor acting on the growth of endothelial cells. Furthermore, MECIF provokes the inhibition of DNA synthesis in endothelial cells to an extent depending on the dose. The powerful action of MECIF is demonstrated by its ability to exert its effects on the growth of 15,000 cells at a concentration as low 10 pg/ml. Furthermore, it has been found that MECIF is specific in its action on cells since it has little effect on the growth of human smooth muscle cells, the fibroblasts of human skin and endothelial cells of pig. These cells were, however, at different stages of reproduction so that the possibility of a different response to MECIF according to the age of the cell cannot be excluded.

The biological effects of MECIF on the growth of human endothelial cells could be partly overcome by the presence of increasing quantities of growth stimulating agents such as ECGF (endothelial cell growth factor) in the test medium.

The purity of MECIF as product was demonstrated by the appearance of a single major protein band in electrophoresis on gel and by a single peak after the passage of MECIF through a chromatographic filtration column on gel of the high performance liquid chromatography type.

The analysis by electrophoresis on gel under nonreduced conditions shows that the major protein band has an apparent molecular weight of 64 kD. MECIF has biological and chemical properties different from those of any known growth regulatory products of monocyte or macrophage origin, such as the interferons (references 18, 19, 20), interleukine-1 (reference 11), TNF (reference 21) or β TGF (reference 22).

MECIF differs from the other known inhibitory factors such as interferons, IL-1, α TNF, TGFβ by its apparent molecular weight. While its action was similar to TGFβ on the growth of endothelial cells, many different features indicate that they are different factors. MECIF is synthetised in the absence of endotoxin stimulation whilst TGFβ requires such stimulation. Reversibility of the endothelial cell growth was easier to be obtained after the exposure of the endothelial cells to MECIF rather than to TGFβ. Antibodies specific against TGFβ. TNFα (Cachetin) and α and γ INF did not neutralize the inhibitory effects of MECIF on the growth of the endothelial cells. The possible contamination of MECIF by tiny amounts of TGFβ appeared unlikely since MECIF preparations at higher concentrations did not affect normal rat kidney fibroblasts proliferation which are classical reference cells for the biological test for TGFβ.

Other endothelial cell growth inhibitory factors of different types of cellular origin, for example those obtained from cartilage (reference 23), vitreous humour (reference 24), platelets (reference 25), or endothelial cells (references 26 and 27) also have different properties from those of MECIF. Summarising, all these studies suggest that MECIF is an endothelial cell inhibitory factor which is different from other inhibitory factors previously identified (references 28 to 30).

Since it was known that monocytes were capable of producing agents promoting the growth of endothelial cells, the maintenance of an equilibrium between the factors promoting growth and the factors inhibiting growth would be very important in a large number of pathophysiological states involving inflammation and atherosclerosis. Moreover, this equilibrium could play a decisive part in the modulation of angiogenesis which may accompany processes of tissue repair, diabetic retinopathies and tumour-related neovascularisation.

Bibliographical References

1. H. Setiadi, F. Lioté and J. L. Wautier. Monocytes and vascular lesions. Nouv. Rev. Fr. Hematol. (1986), 28, 339-343.
2. P. M. Henson, and R. B. Johnston Jr. Tissue injury in inflammation. Oxidants, proteinases, and cationic proteins. J. Clin. Invest. (1987), 79, 669-674.
3. L. Rifas, V. Shen, K. Mitchell, and W. A. Peck. Macrophage-derived growth factor for osteoblast-like cells and chondrocytes. Proc. Natl. Acad. Sci. U.S.A. (1984), 81, 4558-4562.
4. S. J. Leibovich, and R. Ross. A macrophage—dependent factor that stimulates the proliferation of fibroblasts in vitro. Am. J. Pathol. (1976), 84, 501-514.
5. K. C. Glenn, and R. Ross. Human monocyte-derived growth factor(s) for mesenchymal cells: activation of secretion by endotoxin and concanavalin A. Cell. (1981), 25, 603-615.
6. Y. Martinet, P. B. Bitterman, J. F. Mornex, G. R. Grotendorst, G. R. Martin, and R. G. Crystal. Activated human monocytes express the c-sis proto-oncogene and release a mediator showing PDGF-like activity. Nature. (1986), 319, 158-160.
7. P. J. Polverini, R. S. Cotran, M. A. Gimbrone, and E. R. Unanue. Activated macrophages induce vascular proliferation. Nature. (1977), 269, 804-806.
8. G. B. Greenburg, and T. K. Hunt. The proliferative response in vitro of vascular endothelial and smooth muscle cells exposed to wound fluids and macrophages J. Cell. Physiol. (1978), 96, 203-214.
9. R. T. Wall, L. A. Harker, L. J. Quadracci, and G. E. Striker. Factors influencing endothelial cell proliferation in vitro. J. Cell. Physiol. (1978), 96, 203-214.
10. B. M. Martin, M. A. Gimbrone, E. R. Unanue, and R. S. Cotran. Stimulation of nonlymphoid mesenchymal cell proliferation by a macrophage-derived growth factor. J. Immunol. (1981), 126, 1510-1515.
11. B. S. Ooi, E. P. Mc Carthy, A. Hsu, and Y. M. Ooi. Human mononuclear cell modulation of endothelial cell proliferation. J. Lab. Clin. Med. (1983), 102, 428-433.
12. A. Courillon Mallet, J. L. Wautier, and M. P. Wautier. Monocyte-derived endothelial cell inhibitory factor (MECIF). Sixth Inter-Washington Spring Symposium, ed. L. L. GALLO (1986), 160 a (abstract).
13. M. B. Kahaleh, F. De Lustro, W. Bock, and E. D. LeRoy. Human monocyte modulation of endothelial cells and fibroblast growth: possible mechanism for fibrosis Clin. Immunol. Immunopathol. (1986), 39, 242-255.
14. J. L. Wautier, M. P. Wautier, D. Pintigny et al. Factors involved in cell adhesion to vascular endothelium, Blood cells, (1983), 9, 221-234.
15. E. Engvall and P. Perlmann. Enzyme-linked immunosorbent assay (ELISA) III: quantification of specific antibodies by enzyme labelled antiimmunoglobulin in antigen coated tubes. J. Immunol. (1972), 109, 129-135.
16. H. Setiadi, J. L. Wautier, A. Courillon Mallet, P. Passa, and J. P. Caen. Increase adhesion to fibronectin and Mo-1 expression by diabetic monocytes. J. Immunol. (1987), 138, 3230-3234.
17. J. L. Wautier, D. Pintigny, J. Maclouf, M. P. Wautier, E. Corvazier and J. P. Caen. Release of prostacyclin after erythrocyte adhesion to cultured vascular endothelium. J. Lab. Clin. Med. (1986), 107, 210-215.
18. R. Friesel, A. Komoriya, and T. Maciag. Inhibition of endothelial cell proliferation by gamma-interferon. J. Cell. Biol. (1987), 104, 689-696.
19. W. E. Stewart, 2nd. Distinct molecular species of interferons. Virology (1974), 61, 80-86.
20. Y. K. Yip, B. Barrowclough, C. Urban, and J. Vilcek. The molecular weight of human gamma interferon is similar to that of other human interferons. Science (1982), 215, 411-413.
21. L. J. Old. Tumor necrosis factor. Polypeptide mediator network. Nature. (1987), 326, 330-331.
22. R. L. Heimark, D. R. Twardzik and S. M. Schwartz. Inhibition of endothelial regeneration by type-beta transforming growth factor from platelets. Science (1986), 233, 1078-1080.
23. H. Brem, and J. Folkman. Inhibition of tumor angiogenesis mediated by cartilage. J. Exp. Med. (1975) 141, 427-439.

24. L. Raymond, and B. Jacobson. Isolation and identification of stimulatory and inhibitory cell growth factors in bovine vitreous. Exp. Eye. Res. (1982), 34, 267-286.
25. M. T. Brown, and D. R. Clemmons. Platelets contain a peptide inhibitor of endothelial cell replication and growth. Proc. Natl. Acad. Sci. U.S.A. (1986), 83, 3321-3325.
26. C. H. Willems, G.C.B. Asteldi, P. G. De Groot, M. D. Janssen, M. D. Gonsalvez, W. P. Zeijlemaker, J. A. Van Mourik, and W. G. Van Aken. Media conditioned by cultured human vascular endothelial cell inhibit the growth of vascular smooth muscle cells. Exp. Cell. Res. (1982), 139, 191-197.
27. J. J. Castellot Jr., L. V. Faveau, M. J. Karnovsky, and R. D. Rosenberg. Inhibition of vascular smooth muscle cell growth by endothelial cell-derived heparin. Possible role of platelet endoglycosidase J. Biol. Chem. (1982), 257, 11256-11260.
28. R. Crum, S. Szabo, and J. Folkman. A new class of steroids inhibits angiogenesis in the presence of heparin or a heparin fragment. Science (1985), 230, 1375-1378.
29. R. L. Heimark and S. M. Schwartz. The role of membrane-membrane interactions in the regulation of endothelial cell growth. J. Cell. Biol. (1985), 100, 1934-1940.
30. B. L. Schumacher, D. Grant, and R. Eisenstein. Smooth muscle cells produce an inhibitor of endothelial cell growth. Arteriosclerosis. (1985), 5, 110-115.

What is claimed is:

1. A protein which is glycosylated, or glycoprotein with an apparent molecular weight of 64-70 kD, containing 568 amino acid residues distributed in the following proportions: Asp: about 80; Thr: about 23.06; Ser: about 29.40; Glu: about 56.5; Pro: about 27.70; Gly: about 38.98; Ala: about 42.88; Val: about 36.16; Met: about 4.83; Ile: about 18.79; Leu: about 50.92; Tyr: about 20.15; Phe: about 27.16; GlcNH$_2$: about 3.10; Lys: about 60.87; His: about 13.81; Arg: about 27.60, and having the following N-terminal peptide sequence:

Ser-Pro-Glu-Leu-Thr-Phe-Arg-X-Y-Thr-Ile-Serwhere X and Y, which may be identical or different, each represent Trp or Asp.

2. A protein which is glycosylated, or glycoprotein according to claim 1 with an apparent molecular weight of 66 kD.

3. A pharmaceutical composition comprising as active principle, an effective amount of the glycoprotein of claim 1 in association with a pharmaceutically acceptable carrier.

4. A therapeutic composition comprising as active principle, an effective amount of the glycoprotein according to claim 2 in association with a pharmaceutically acceptable carrier.

* * * * *